US006956136B2

(12) United States Patent
Dyckman et al.

(10) Patent No.: US 6,956,136 B2
(45) Date of Patent: Oct. 18, 2005

(54) METHOD OF PRODUCING CUMENE HYDROPEROXIDE

(75) Inventors: Arkady Samuilovich Dyckman, Saint Petersburg (RU); John William Fulmer, Mt. Vernon, IN (US); Viktor Vladimirovich Pinson, Saint Petersburg (RU); Andrey Vladimirovich Zinenkov, Saint Petersburg (RU); Boris Issakovich Gorovits, St. Petersburg (RU)

(73) Assignee: General Electric Company, Schenectady, NY (US)

( * ) Notice: Subject to any disclaimer, the term of this patent is extended or adjusted under 35 U.S.C. 154(b) by 11 days.

(21) Appl. No.: 10/629,189

(22) Filed: Jul. 29, 2003

(65) Prior Publication Data

US 2004/0059162 A1 Mar. 25, 2004

(30) Foreign Application Priority Data

Jul. 29, 2002 (RU) ...................................... 2002120653

(51) Int. Cl.$^7$ ............................................ C07C 409/10
(52) U.S. Cl. ...................... 568/558; 568/568; 568/569; 568/577
(58) Field of Search ................................ 568/558, 568, 568/569, 577

(56) References Cited

U.S. PATENT DOCUMENTS

| | | | |
|---|---|---|---|
| 2,577,768 A | | 12/1951 | Joris |
| 2,613,227 A | | 10/1952 | Joris |
| 2,619,509 A | | 11/1952 | Joris |
| 2,632,026 A | | 3/1953 | Conner, Jr. |
| 2,632,774 A | | 3/1953 | Conner, Jr. |
| 2,689,936 A | | 9/1954 | Kirsch et al. |
| 3,187,055 A | | 6/1965 | Armstrong et al. |
| 3,417,158 A | * | 12/1968 | Forry, Jr. et al. ........... 585/899 |
| 3,523,977 A | | 8/1970 | Reni et al. |
| 3,907,901 A | | 9/1975 | Feder et al. |
| 3,933,921 A | | 1/1976 | Suda et al. |
| 4,008,290 A | | 2/1977 | Ward ...................... 260/672 T |
| 4,051,191 A | | 9/1977 | Ward ...................... 260/671 R |
| 4,153,635 A | | 5/1979 | Wu et al. |
| 4,192,952 A | | 3/1980 | Stueben |
| 4,283,568 A | | 8/1981 | Pujado ........................ 568/754 |
| 4,329,514 A | * | 5/1982 | van der Weijst et al. ... 568/577 |
| 4,343,957 A | | 8/1982 | Sartorio et al. ............. 585/449 |
| 5,120,902 A | | 6/1992 | Tagamolila et al. |
| 5,220,103 A | | 6/1993 | Tagamolila et al. |
| 5,530,166 A | | 6/1996 | Zakoshansky et al. ...... 568/798 |
| 5,767,322 A | * | 6/1998 | Zakoshansky et al. ...... 568/571 |
| 5,908,962 A | * | 6/1999 | Zakoshansky et al. ...... 568/571 |
| 6,077,977 A | | 6/2000 | Gopinathan et al. |
| 6,465,695 B1 | * | 10/2002 | Fulmer et al. .............. 568/571 |
| 6,620,974 B2 | * | 9/2003 | Fulmer et al. .............. 568/571 |

OTHER PUBLICATIONS

USSR Author's Certificate 567723, published on Sep. 9, 1977 in Bulletin of Inventions No. 29.

www.uop.com. "Aromatics and Derivatives, Cyclar Process". pp. 1–3. (2001).

Klaus Weissermel. Industrial Organic Chemistry, Third Completely Revised Edition, VCH, pp. 312–324, 342–343, 353–355, 358–359.

* cited by examiner

Primary Examiner—Rosalynd Keys

(57) ABSTRACT

The specification provides a method of producing cumene hydroperoxide by continuous aqueous-emulsion oxidation at a high temperature and pressure in a cascade of reactors, wherein the process is conducted in the presence of a mixture of an aqueous solution of an ammonium salt with a concentration of 0.001–0.5 mass % and an aqueous solution of ammonia with a concentration of 0.001–0.5 mass %, which mixture is fed into each oxidation reactor in an ammonia:ammonium salt mass ratio of 1:100 to 100:1.

18 Claims, 1 Drawing Sheet

METHOD OF PRODUCING CUMENE HYDROPEROXIDE

The present application is a U.S. non-provisional application based upon and claiming priority from Russian Application No. 2002120653/04 (021637), with a filing date of Jul. 29, 2002, as amended on Jun. 11, 2003, which is hereby incorporated by reference.

BACKGROUND OF THE INVENTION

This invention relates to the field of petrochemical synthesis, i.e. to the technology of oxidation of cumene by an oxygen-containing gas (usually by air) to form cumene hydroperoxide (CHP) whose subsequent decomposition in the presence of an acid affords phenol and acetone. These reactions are the typical scheme for industrial heavy-tonnage production.

Two primary methods of producing cumene hydroperoxide (CHP) are known.

The first, so-called "dry" method is based on liquid phase oxidation of pure) cumene conducted in the presence of catalytic amounts of basic compounds, e.g.:
carbonates of alkali and alkaline-earth metals [See, e.g., U.S. Pat. No. 2,613,227 (1952), U.S. Pat. No. 2,619,509 (1952), U.S. Pat. No. 2,689,936 (1954)],
sodium bicarbonate [See, e.g., U.S. Pat. No. 2,577,768 (1951)],
calcium hydroxide [See, e.g., U.S. Pat. No. 2,632,774 (1953)],
barium oxide [See, e.g., U.S. Pat. No. 4,153,635 (1979)],
substituted ammonium salts [See, e.g., U.S. Pat. No. 4,192,952 (1980)], and other compounds that, in the process of oxidation, are suspended in cumene.

The use of such basic compounds is advantageous for the following reasons. In the process of oxidation of cumene, trace amounts of organic acids, particularly formic acid, are formed along with the target product, CHP, and two main impurities, acetophenone (ACP) and dimethylphenylcarbinol (DMPC). The presence of formic acid in the cumene oxidation reaction mass inevitably leads to acid-catalytic decomposition of CHP with formation of phenol and acetone. It is known that phenol is a strong inhibitor of the free-radical oxidation of alkylaromatic hydrocarbons and cumene in particular. Thus, the presence of even trace amounts of formic acid significantly slows the oxidation process rate. Therefore, efforts are made to conduct the cumene oxidation reaction at pH~5–7. The most obvious technique for removing acids from the cumene oxidation reaction mass is to conduct this process in the presence of the aforementioned advantageous basic compounds.

The second, so-called "wet," aqueous-emulsion method of producing cumene hydroperoxide by oxidation of cumene consists of conducting the oxidation reaction in a three-phase system including:
an organic phase consisting of cumene and the products of its oxidation,
an aqueous phase consisting of solutions of basic compounds, and
a gaseous phase consisting of an oxygen-containing gas (usually air).

Both the "dry" and the "wet" cumene oxidation methods are conducted in the presence of basic compounds.

Basic compounds dissolve in water much better than in hydrocarbons. Therefore, the mass transfer process in heterogeneous "organic phase—water" systems is much more effective than in "organic phase—solid dispersion" systems. So, in terms of the more complete and faster removal of acids from the system, the "wet" oxidation method should be recognized as more effective than the "dry" method.

This invention specifically relates to the "wet" method of cumene oxidation.

A method is known for producing CHP by oxidation of cumene by air at a high temperature. The oxidation reaction is conducted in the presence of ammonium salts of organic acids or carbonic acid; 0.05–50% aqueous solutions of the salts are used. The method (USSR Author's Certificate No. 567723, published on Sep. 9, 1977 in Bulletin of Inventions No. 29) has the following disadvantages, which are first discuss whit examples using ammonium salts of organic acids. Under high-temperature (80–120° C.) conditions of the cumene oxidation process, partial thermal decomposition of the salts occurs by the following reaction:

$$NH_4A \xrightarrow{H_2O} NH_3\uparrow + AlH$$

where:
A is the symbol of an organic anion,
AH is the symbol of the acid of that organic anion.

Since ammonia features a significant volatility, the liquid phase predominantly contains the acid that inhibits the cumene oxidation process. Moreover, it is economically inefficient to use ammonium salts of such relatively expensive organic acids as ethylenediaminetetraacetic or 1,10-decanedicarbonic acid.

If ammonium carbonate, an ammonium salt of carbonic acid, is used, then under high-temperature conditions, decomposition of the salt occurs according to the following reaction mechanisms:

$$(NH_4)_2CO_3 \rightleftharpoons 2NH_3\uparrow + CO_2\uparrow + H_2O \quad (1)$$

$$(NH_4)_2CO_3 \underset{-H_2O}{\rightleftharpoons} H_2N-C\overset{O}{\underset{ONH_4}{\diagdown}} \underset{-H_2O}{\rightleftharpoons} H_2N-C\overset{O}{\underset{NH_2}{\diagdown}} \quad (2)$$

ammonium carbamate      carbamide

Reaction (1) predominately occurs in the aqueous phase while reaction (2) dominates in the organic phase.

An increase in the temperature shifts the equilibrium in Reaction (1) to the right while a decrease in the temperature shifts it to the left. Industrial cumene oxidation reactors are equipped with condensation systems whose function is to condense the carryover vapors of cumene and, partially, of water. In the condensation process that is conducted under lower temperature conditions, the equilibrium in Reaction (1), as mentioned above, shifts to the left, which results in a partial recovery of the alkaline agent in the cumene oxidation reactor. That circumstance has a positive effect on the process performance. On the other hand, Reaction (2) eventually leads to formation of carbamide (urea) whose aqueous solution has a much lower pH than the corresponding ammonia solutions. That circumstance inevitably leads to a worsening of the characteristics (rate and selectivity) of the oxidation process.

Furthermore, the salts are practically insoluble in organic phases while the volume of the organic phase represents the larger part of the solution. That is why the salts clog the pipelines and precipitate on the walls of heat-exchanging equipment, which leads to reduced heat transfer coefficients. This circumstance especially impairs the process of CHP rectification/concentration that follows the cumene oxidation step.

As follows from the description of invention (Author's Certificate No. 567723), that process is essentially a "dry" oxidation process since the amounts of the aqueous solutions added are so small (e.g., 50% solutions of ammonium carbonate are used in an amount of 0.17 g per 300 g of cumene) that all water is dissolved.

A process is known for producing cumene hydroperoxide using air oxygen in the presence of gaseous ammonia in the amount of no less than 0.5% of the reacted oxygen [U.S. Pat. No. 2,632,026 (1953)]. Although the cumene conversion (up to 21%) and CHP formation selectivity (up to 97.3%) characteristics of that process are good, its primary disadvantage is a very low oxidation rate.

The process has the following primary disadvantage: in feeding gaseous ammonia into the reactor, most of the ammonia escapes into the atmosphere. All existing CHP synthesis plants are equipped with waste-gas afterburning units (thermal afterburning units are used more often than the catalytic ones). This, in turn, leads to the presence of nitrogen oxides in the gaseous emissions and has a negative environmental impact. Furthermore, the patent's high conversion and selectivity characteristics are achieved at a very low cumene oxidation rate (0.6% cumene per hour). In its technical essence, the closest prototype of the proposed method is a process for producing cumene hydroperoxide by oxidation of cumene in an aqueous/alkaline emulsion at a temperature of 92–107.2° C. and a gage pressure of 5 atm in a horizontal cascade of reactors (no fewer than two) in two steps: cumene sequentially passes the first-step and second-step reactors into each of which the oxidant (air) is fed. In order to neutralize the acids, an aqueous solution of sodium carbonate is fed into the second step of the process; in the course of neutralization, sodium carbonate is transformed into sodium bicarbonate. The aqueous salt solution from the second step of the process is treated by ammonia or ammonium hydroxide up to pH=10.5–11.5; in the course of that process, sodium bicarbonate is transformed into the mixed salt, $NH_4NaCO_3$. The neutralized solution is fed into the first-step reactors in a ratio of (3.5–2.6):1 to the cumene that is fed for oxidation [U.S. Pat. No. 5,767,322, 1998: prototype].

U.S. Pat. No. 5,908,962, 1999, held by the same applicant, proposes, under the conditions similar to U.S. Pat. No. 5,767,322, feeding ammonia in an amount at least stoichiometric in relation to the amount of acids formed in the cumene oxidation process while monitoring the salts thus formed under ambient pH of 10.0–12.0 while ammonia is injected directly into the first-step reactors.

It is known that, in oxidation of cumene, two byproducts, dimethylphenylcarbinol (DMPC) and acetophenone (ACP), are formed along with CHP; the amount of those byproducts determines, ultimately, the yield of commercial products and the mass of the undesirable production waste, the phenolic resin; it also complicates the process of producing commercial products of the required quality. Therefore, an improvement of the cumene oxidation selectivity at a sufficiently high conversion (optimal CHP concentration in the flow leaving the oxidation unit is 25–30%) is an important issue for increasing the effectiveness of the industrial technology.

The following disadvantages of the prototype process can also be indicated:

using different neutralizing solutions for the first and second oxidation steps, which complicates the technological scheme;

the presence of sodium salts, which can precipitate on the walls of heat-exchanging equipment;

leads to reduced heat transfer coefficients;

furthermore, the large amount of the neutralizing aqueous solution in relation to the cumene that is being oxidized, (3.5–2.6):1. Providing for a required capacity of the oxidation plant results in larger reactor volumes compared to the "dry" oxidation method.

SUMMARY OF INVENTION

The aim of this invention is to simplify the technology while maintaining the high selectivity and rate of cumene oxidation without impairing the environmental characteristics of the process. This aim is achieved by producing cumene hydroperoxide in a series of oxidation reactors wherein the process is conducted in the presence of a mixture of an aqueous solution of an ammonium salt having a concentration of 0.001–0.5 mass % and an aqueous solution of ammonia having a concentration of 0.001–0.5 mass %, which mixture is fed into each oxidation reactor in an ammonia:ammonium salt mass ratio of between 1:100 to 100:1.

A method of producing cumene hydroperoxide, comprises: forming ammonium salt by reacting carbon dioxide with ammonia in the presence of an arqueous feed stream, and reacting oxygen with cumene by passing the oxygen through a water-cumene emulsion in a presence of a mixture of the ammonium salt and ammonia. The mixture is fed in an ammonia:ammonium salt mass ratio of between 1:100 to 100:1.

DETAILED DESCRIPTION

Figure 1:
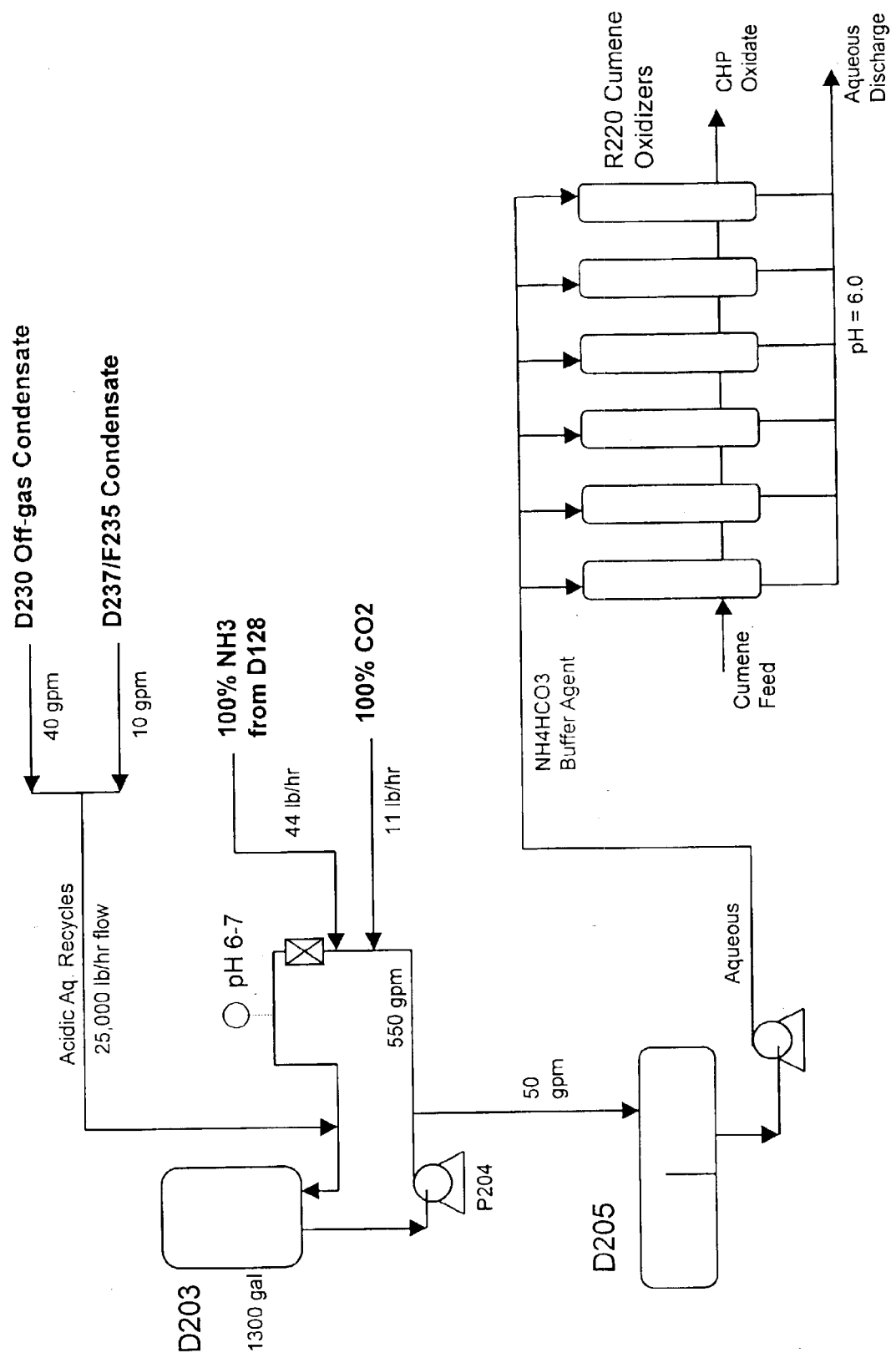
FIG. 1 is a schematic illustration of an apparatus employed in a cumene oxidation method of producing cumene hydroperoxide.

The process of continuous aqueous-emulsion oxidation of cumene is preferably conducted in a cascade of flow-through reactors by bubbling air through a water-cumene emulsion. The process is conducted at a temperature of 80–120° C. in a first oxidation reactor of the series of oxidation reactors with a gradual decrease to 80–90° C. in a last oxidation reactor of the series of oxidation reactors and at a gage pressure of up to 5 atm. For example, the process is conducted at a temperature of 120° C. in the first reactor, lowering it to 80° C. in the last reactor, and at a gage pressure of 5 atm, in the presence of a mixture consisting of a 0.007–0.5% aqueous solution of ammonia and a 0.001–0.5 mass % solution of an ammonium salt (e.g., ammonium bicarbonate, ammonium carbonate, ammonium carbamate or a mixture thereof). The ammonia: ammonium salt mass ratio is (1:100):(100:1), preferably (1:10):(10:1). The oxidative feedstock is fed into the bottom part of each reactor while the aqueous phase is fed into the top part of each reactor. The organic layer of the reaction mass gravity overflows into a vessel, from which it is periodically discharged. The aqueous phase is periodically discharged from the bottom of the reactor and flows through valves into a vessel. The gaseous phase is partially condensed in a cooler, passes an activated-coal filter, where partial sorption of cumene takes place, and then goes, through control valves, into an oxygen analyzer and rheometer. The discharge rates of the liquid phases are controlled by pumps. The reactor temperature is set by a thermostat (oil is used as a hear-carrying agent) and measured by a thermocouple.

An essential distinctive feature of the proposed aqueous-emulsion process of cumene oxidation is that the process is conducted using a mixture consisting of a 0.001–0.5 mass % aqueous solution of ammonia and a 0.001–0.5 mass % solution of an ammonium salt (ammonium bicarbonate, ammonium carbonate, ammonium carbamate or a mixture thereof) at an ammonia:ammonium salt mass ratio of (1:100):(100:1), preferably (1:10):(10:1).

The utilization of ammonium salts such as ammonium bicarbonate as neutralizing agents in the cumene oxidation process makes it possible to substantially simplify the process technology, at a process selectivity of ~94% or better and a conversion of 23%, by excluding the use of neutralizing agents that form solid deposits on heat-exchanging equipment.

A representative apparatus for practicing the process according to the invention is shown in FIG. 1.

The industrial applicability of the proposed method is confirmed by the following examples.

EXAMPLES 1–6

The basic experiment parameters (a pressure of 5 atm and a temperature of 80–120° C.) simulate the working conditions of the individual reactors of an actual industrial plant. The feedstock flow rate was selected in such a manner that the CHP concentration gain corresponded to a six-reactor system.

In the experiments, cumene of a purity of no less than 99.85% was used. The aqueous phase was prepared from ammonium bicarbonate of the "chemically pure" grade with an ammonia content of no less than 21.7%.

In order to simulate the operation of an actual six-reactor industrial plant, temperatures falling into the range of 120–87.8° C. were selected (see Table 1). For the first reactor (T=120° C.), pure commercial cumene ($C_{CHP.0}$= 0.07%) was used as the oxidative feedstock. In the subsequent experiments, the products obtained in the course of the previous experiment were used as feedstock.

The experiments were conducted as follows. In the atmosphere of nitrogen, the reactor was filled, until liquid overflowed into the vessel, with the oxidative feedstock and 20 ml of the 0.001–0.5 mass % aqueous solution of the ammonium salt and the reactor heating was turned on. After the required temperature was reached, the nitrogen flow was stopped and air feeding was started. In 1 hour, the first sample of the organic phase was taken through a siphon tube and analyzed for CHP content. In another hour, the second sample was taken and sampling was done in that manner until the expected CHP concentration was reached. After that, the pumps were turned on and in 12–15 hours the steady mode was established. The aqueous phase was periodically (every 0.5 hours) discharged from the bottom of the reactor. The organic phase was continuously overflowing into a receiving vessel that was discharged periodically. After a steady mode was reached, organic phase samples were taken every 3–4 hours and analyzed for the content of CHP (titration) as well as the contents of DMPC and ACP (gas-liquid chromatography). The duration of each experiment was 24 to 72 hours.

The ammonium salt concentration for each of the experiments was selected experimentally. It has been found that, for each of the simulated reactors, there exists an optimal concentration below which the oxidation reaction rate falls significantly while, at higher concentrations, a decrease in selectivity is observed.

The data thus obtained for experiments 1–6 respectively are shown in

TABLE 1

| T ° C. | Concentration, mass % | | | | Cumene conversion, % | Selectivity of CHP formation, % | pH of aqueous phase | pH of org. phase |
| --- | --- | --- | --- | --- | --- | --- | --- | --- |
| | Ammonium salt | Ammonia | $C_{CHP.0}$, % | $C_{CHP}$, % | | | | |
| 120.0 | 0.001 | 0.005 | 10.07 | 6.41 | 5.23 | 95.6 | 6.7 | 6.2 |
| 102.0 | 0.005 | 0.007 | 6.41 | 11.62 | 5.01 | 95.0 | 6.9 | 6.3 |
| 98.0 | 0.015 | 0.005 | 11.62 | 17.63 | 4.76 | 94.7 | 7.0 | 6.9 |
| 94.4 | 0.03 | 0.05 | 17.63 | 22.20 | 3.80 | 94.0 | 7.3 | 6.4 |
| 91.0 | 0.08 | 0.02 | 22.20 | 24.75 | 2.48 | 92.7 | 7.2 | 6.3 |
| 80.0 | 0.04 | 0.08 | 24.75 | 28.8 | 3.40 | 92.5 | 7.3 | 6.3 |

The oxidative feedstock for each of the experiments was either pure commercial cumene (first reactor, T=120° C.) or oxidation products obtained in the course of the previous experiments.

The concentration of CHP was determined by iodometric titration.

The concentrations of ACP and DMPC were determined by gas-liquid chromatography: a chromatograph with a flame ionization detector and a 25 m long column with an outer diameter of 0.32 mm; stationary liquid phase: OV-1; $T_{initial}$=50° C., temperature rising rate: 8° C./min, $T_{final}$=20° C. The quantitative calculations were performed using n-pentadecane as the internal standard.

The aqueous phase flowrate was 6–7 ml/hr while the oxidative feedstock flowrate was 200–260 ml/hr.

EXAMPLE 7

The process is conducted similarly to examples 1–6 but, in oxidation, an aqueous solution of an ammonium salt obtained by passing carbon dioxide gas through an aqueous solution of ammonia is used. At an oxidation temperature of 120° C. and a pressure of 5 atm, the conversion is 5.3% and the selectivity was 85.7%.

What is claimed is:

1. A method of producing cumene hydroperoxide comprising:
    reacting in a series or oxidation reactors oxygen with cumene by passing the oxygen through a water-cumene emulsion in a presence of a mixture of an aqueous solution of an ammonium salt with a concentration of 0.001–0.5 mass % based upon a total mass of the aqueous solution of the ammonium salt and an aqueous solution of ammonia with a concentration of 0.001–0.5 mass % bused upon a total mass of the arqueous solution of the ammonia, wherein the mixture is fed into each oxidation reactor of the series of oxidation reactors in an ammonia:ammonium salt mass ratio of between 1:100 to 100:1;

wherein the ammonium salt is selected from the group consisting of ammonium bicarbonate, ammonium carbonate, ammonium carbamate, and a mixture thereof.

2. A method according to claim 1, wherein the method is conducted at a temperature of 100–120° C. in a first oxidation reactor of the series of oxidation reactors with a gradual decrease to 80–90° C. in a last oxidation reactor of the series of oxidation reactors and at a gage pressure of up to 5 atm.

3. The method according to claim 1, further comprising forming the ammonium salt by reacting carbon dioxide with ammonia in the presence of an aqueous feed stream for one of the oxidation reactors of the series of oxidation reactors.

4. The method according to claim 1, wherein the ammonia:ammonium salt mass ratio is 1:10 to 10:1.

5. The method according to claim 1, wherein the oxygen is from air.

6. A method of producing cumene hydroperoxide comprising:

reacting in a series of oxidation reactors oxygen with cumene by passing the oxygen through a water-cumene emulsion in a presence of a mixture of an aqueous solution of an ammonium salt with a concentration of 0.001–0.5 mass % based upon a total mass of the aqueous solution of the ammonium salt and an aqueous solution of ammonia with a concentration of 0.001–0.5 mass % based upon a total mass of the aqueous solution of the ammonia, wherein the mixture is fed into each oxidation reactor of the series of oxidation reactors in an ammonia:ammonium stilt mass ratio of 1:10 to 10:1, wherein the method is conducted at a temperature of 100–120° C. in a first oxidation reactor of the series of oxidation reactors with a decrease to 80–90° C. in a last oxidation reactor of the series of oxidation reactors and at a gage pressure of up to 5 atm, and wherein the ammonium salt is selected from the group consisting of ammonium bicarbonate, ammonium carbonate, ammonium carbamate, and a mixture thereof.

7. A method of producing cumene hydroperoxide, comprising:

forming ammonium salt by reacting carbon dioxide with ammonia in the presence of an arqueous feed stream; and reacting oxygen with cumene by passing the oxygen through a water-cumene emulsion in a presence of mixture of the ammonium salt and the ammonia;

wherein the mixture is fed in an ammonia:ammonium salt mass ratio of 1:100 to 100:1.

8. The method according to claim 7, wherein the ammonium salt is selected from the group consisting of ammonium bicarbonate, ammonium carbonate, ammonium carbamate, or a mixture thereof.

9. The method according to claim 7, wherein the ammonium salt comprises ammonium carbamate.

10. The method according to claim 7, wherein the ammonia:ammonium salt mass ratio is 1:10 to 10:1.

11. The method according to claim 7, wherein the method is conducted at a temperature of 100–120° C. in a first oxidation reactor with a gradual decrease to 80–90° C. in a last oxidation reactor, and at a gage pressure of up to 5 atm.

12. The method according to claim 7, wherein the mixture of the ammonium salt and ammonia comprises an aqueous solution of the ammonium salt with a concentration of 0.001–0.5 mass % based upon a total mass of the aqueous solution of the ammonium salt, and an aqueous solution of the ammonia with a concentration of 0.001–0.5 mass % based upon a total mass of the aqueous solution of the ammonia.

13. The method according to claim 7, wherein the reacting of the oxygen with the cumene is in the absence of a neutralizing agent that forms a solid deposit on heat-exchanging equipment.

14. The method according to claim 13, wherein the neutralizing agent comprises sodium salt.

15. The method according to claim 1, wherein the reacting of the oxygen with the cumene is in tho absence of a neutralizing agent that forms a solid deposit on heat-exchanging equipment.

16. The method according to claim 14, wherein the neutralizing agent comprises sodium salt.

17. The method according to claim 1, further comprising forming the ammonium salt by reacting carbon dioxide with the ammonia.

18. The method according to claim 1, wherein the ammonium salt is ammonium carbamate.

* * * * *